United States Patent
Nordin et al.

(10) Patent No.: US 7,189,362 B2
(45) Date of Patent: Mar. 13, 2007

(54) OPTICAL WAVEGUIDE MICROCANTILEVER WITH DIFFERENTIAL OUTPUT AND ASSOCIATED METHODS OF CANTILEVER SENSING

(75) Inventors: Gregory Nordin, Huntsville, AL (US); Jaime Cardenas Gonzalez, Charlotte, NC (US); Michael A. George, Huntsville, AL (US)

(73) Assignee: University of Alabama in Huntsville, Huntsville, AL (US)

( * ) Notice: Subject to any disclaimer, the term of this patent is extended or adjusted under 35 U.S.C. 154(b) by 263 days.

(21) Appl. No.: 10/793,983

(22) Filed: Mar. 5, 2004

(65) Prior Publication Data

US 2005/0195407 A1    Sep. 8, 2005

(51) Int. Cl.
| | |
|---|---|
| *B32B 5/02* | (2006.01) |
| *B32B 27/04* | (2006.01) |
| *C12Q 1/68* | (2006.01) |
| *G01N 21/00* | (2006.01) |
| *G01N 15/06* | (2006.01) |

(52) U.S. Cl. ............... 422/82.11; 422/50; 422/55; 422/56; 422/57; 422/58; 422/68.1; 422/82.05; 422/82.09; 436/43; 436/63; 436/164; 436/169; 436/172; 356/73.1

(58) Field of Classification Search ............ 422/50, 422/55, 56, 57, 58, 68.1, 82.05, 82.09, 82.11; 436/43, 63, 164, 169, 172
See application file for complete search history.

(56) References Cited

U.S. PATENT DOCUMENTS

| 5,719,324 A | 2/1998 | Thundat et al. |
|---|---|---|
| 5,891,747 A | 4/1999 | Farah |

(Continued)

OTHER PUBLICATIONS

Jianhua Jiang and Gregory P. Nordin; A Rigorous Unidirectional Method For Designing Finite Aperture Diffractivee Optical Elements; Optics Express; Sep. 11, 2000; vol. 7, No. 6.

(Continued)

*Primary Examiner*—Brian Sines
(74) *Attorney, Agent, or Firm*—Thomas Kayden Horstemeyer & Risley, L.L.P.

(57) ABSTRACT

A microcantilever sensing system includes a waveguide cantilever that permits an optical signal to propagate through an endface of the cantilever. The propagated signal is received by a receiver waveguide across a gap from the cantilever. The receiver waveguide provides the optical signal to a differential beamsplitter. The signal is differentially split according to the position of the optical signal incident upon the receiving waveguide. A method of determining a deflection waveguide microcantilever is also disclosed. An optical signal is transmitted from the endface of a waveguide microcantilever and received by the receiver waveguide. The optical signal is differentially split and then each split signal is compared to determine beam deflection. A method of fabricating a microcantilever sensor provides a differential beamsplitter in optical communication with a waveguide cantilever.

40 Claims, 4 Drawing Sheets

U.S. PATENT DOCUMENTS

| | | | |
|---|---|---|---|
| 6,094,289 | A | 7/2000 | Moranski et al. |
| 6,392,233 | B1 | 5/2002 | Channin et al. |
| 6,525,307 | B1 | 2/2003 | Evans, III et al. |
| 6,575,020 | B1 * | 6/2003 | de Charmoy Grey et al. .................... 73/54.23 |
| 6,987,898 | B2 * | 1/2006 | Tran et al. ..................... 385/13 |
| 2005/0018946 | A1 | 1/2005 | Tran et al. |

OTHER PUBLICATIONS

Jianhua Jiang, Jingbo Cai, Gregory P. Nordin and Lixia Li; Parallel Microgenetic Algorithm Design for Photonic Crystal and Waveguide Structures; Optics Letters; Dec. 1, 2003; vol. 28, No. 23.

Ollier, et al., "Micro-Opto Mechanical Vibration Sensor Integrated on Silicon," Journal of Lightwave Technology, vol. 17, No. 1, Jan. 1999.

Wu, et al., "Integrated Optical Sensors Using Micromechanical Bridges and Cantilevers,"Delft Univ. of Technology, Dept. of Applied Physics, SPIE vol. 1793, Integrated Optics and Microstructures (1992)/83.

Muller, et al., "Technological Processes and Modeling of Opto-Electro-Mechanical Microstructures," Materials Science in Semiconductor Processing 3 (2000) 427-431.

Burcham, et al., "Micromachined Silicon Cantilever Beam Accelerometer Incorporating an Integrated Optical Waveguide," University of Cincinnati, Department of Electrical and Computer Engineering, SPIE vol. 1793 Integrated Optics and Microstructures (1192).

A.V. Churenkov, "Silicon Micromechanical Optical Waveguide for Sensing and Modulation," Sensors and Actuators A 57 (1996) 21-27.

* cited by examiner

OPTICAL WAVEGUIDE MICROCANTILEVER WITH DIFFERENTIAL OUTPUT AND ASSOCIATED METHODS OF CANTILEVER SENSING

FIELD OF THE INVENTION

The invention relates to microcantilever sensing systems, cantilever sensing methods, and fabrication methods and, more particularly, to microcantilever sensing systems having a waveguide cantilever and methods of cantilever sensing using waveguide cantilever.

BACKGROUND OF THE INVENTION

Microcantilever chemical and biological sensors operate by undergoing specific changes upon interactions with analytes. One great advantage of the cantilever technique is that five response parameters (resonance frequency, phase, amplitude, Q-factor, and deflection) can be simultaneously detected. The resonance frequency, f, of an oscillating microcantilever can be expressed as:

$$f = \frac{1}{2\pi}\sqrt{\frac{k}{m^*}} \quad (1)$$

where k is the spring constant of the lever and m* is the effective mass of the microcantilever. The effective mass can be related to the mass of the beam, $m_b$, through the relation $m^* = nm_b$, where n is a geometric parameter. Typical values for n are 0.14 for a v-shaped cantilever and 0.24 for a rectangular cantilever. Both changes in the effective mass and changes in the spring constant can affect the resonance frequency.

The spring constant can also change due to adsorption processes in which a substance is taken upon the surface of a cantilever which changes the mass and surface stress of the cantilever, resulting in a change in resonance of the cantilever. To account for this, Eq. (1) can be modified as:

$$f_2 = \frac{1}{2\pi}\sqrt{\frac{k+\delta K}{m^* + n\delta m}} \quad (2)$$

where the initial resonance frequency $f_1$, changes to $f_2$ due to adsorption. In this equation, k changes to k+δk as a result of adsorption induced surface stress while m* changes to m*+nδm due to mass loading. Surface stress on the top and bottom of the cantilever (denoted by $s_1$, and $s_2$) are balanced at equilibrium. Upon differential adsorption on the two surfaces, they can become unequal and cause bending of the cantilever. The change in the spring constant due to surface stress is given by:

$$\delta k = \frac{\pi^2 n}{4n_1}(\delta s_1 + \delta s_2) \quad (3)$$

where $n_1$ is a geometric factor for v-shape cantilevers, and $\delta s_1 = (s_1 - s'_1)$ and $\delta s_2 = (s_2 - s'_2)$ are changes in surface stress on the top and the bottom surface of the cantilever before and after adsorption. Adsorption induced changes in the surface stress on one side of the microcantilever results in measurable bending or static deflection of the microcantilever, which can be employed as a transduction or sensing mechanism. A sensing microcantilever can be created by applying a thin chemoselective coating to one side of the cantilever to take up a selected chemical compound and produce the change in cantilever resonance.

Static bending can be pronounced and measurable, however, in most cases, changes in k and m due to adsorption are small. The resonance frequency after adsorption can be approximated by Eq. (4)

$$f_2 = f_1\left[1 + \frac{1}{2}\left(\frac{\delta k}{k} - \frac{\delta m^*}{m^*}\right)\right] \quad (4)$$

and is valid as long as $\delta m \ll m_b$ and $\delta k \ll k$:

Thermally induced oscillations have been exploited to study cantilever properties including the spring constant and Q. This method takes advantage of the equipartition theorem applied to cantilever potential energy:

$$\left\langle \frac{1}{2}mf_o x^2 \right\rangle = \frac{1}{2}k_B T \quad (5)$$

where $f_o$ is the resonant frequency, $k_B$ is Boltzman's constant, m is the mass, T the absolute temperature, and $x^2$ is the mean squared cantilever displacement in any one mode. The mean squared displacement is available from an integral under the square of the power spectral curve. The spring constant is obtained by:

$$k = k_B T / \langle x^2 \rangle \quad (6)$$

Thermal resonance frequency and the spring constant can be obtained as mentioned above by acquiring the power spectrum for the resonance using the frequency modulation method.

For a sensor that depends on vapor sorption processes, the chemical interface between the transducer and ambient air is a vital aspect in its successful operation. It is standard procedure to coat microcantilevers on one side to enhance sensitivity and induce chemical selectivity through the choice of coating material. For example in the case of hazardous vapor sensors, microcantilevers have been coated with 1–10 nm of a chemoselective polymer. These are usually polymers that readily experience sorption in the presence of the analyte and undergo changes such as inhomogeneous swelling as the molecules are adsorbed. Swelling results in deflection of the cantilever and a change in its resonance frequency. The cantilever/coating system acts as a molecular recognition system in which the sensing function is manifested as a change in the cantilever's state and/or properties. Similarly, sensors for biomolecules are easily functionalized on the gold side of a gold-coated microcantilever via dipping the cantilevers in solutions containing tethering molecules such as thiol-groups. Depending on the choice of receptor molecule, the cantilever can be used to detect specific proteins, DNA segments, and other biomolecules.

Many polymer-toxic vapor systems that are useful for sensor applications have been identified by researchers. These materials have been identified by examining the response of a coated surface acoustic wave sensor exposed to a particular analyte. The response depends on a partitioning phenomena in which the partition coefficient, B, represents the equilibrium vapor-polymer solubility at a given temperature. The partition coefficient measures the overall strength of interaction and is equal to $C_p/C_v$ where $C_v$ is the vapor concentration in the gas phase, while $C_p$ is the concentration in the polymer. Larger values of B indicate stronger interactions. The values of B for various polymer-toxic vapor systems can be obtained through gas-liquid chromatographic (GLC) analysis.

Chemoselective polymers have been tailored for enhanced sorption of molecular species by increasing the active surface area as well as by considering coating-vapor solubility interactions. Specifically, polymer-vapor systems that experience weaker, reversible interactions at ambient temperatures (e.g. hydrogen bonding, dispersion, and dipole-dipole interactions) have been optimized while systems that tend to form strong irreversible covalent bonds have been avoided. A class of polymer coatings and corresponding molecular sorbents have been developed that undergo spontaneous regeneration at room temperature after the vapor is removed from the ambient.

Various methods are employed to coat cantilevers including the use of nanoinjectors, microspray methods, and functionalization by dipping the cantilevers in a reagent to produced adsorbed layers such as self-assembled monolayers (SAMs). The choice of the process of coating microcantilevers is dependent upon the nature of the coating being employed. Moreover, in the case of microcantilever arrays a coating method is required that permits individual microcantilevers to have a unique coating compared to the other microcantilevers in the array.

In one deposition method, self-assembled monolayers (SAMs) of molecules such as alkanethiols are formed on the gold-coated side of microcantilevers to detect a wide variety of analytes in both liquid and vapor environments. SAMs have been developed for different sensing applications including metal ions in water and vapors of explosive chemicals such as trinitrotoluene (TNT) and cyclotrimethylenetrinitramine (RDX). Since SAMs are deposited by dipping cantilevers in a reagent, an approach is needed to coat unique SAMs on individual microcantilevers in an array. This deposition technique has been demonstrated using micro-capillaries, and the resultant functionalized microcantilever array was used for label-free detection of two cardiac biomarker proteins. SAMs represent one path toward the functionalization of individual microcantilevers in an array as long as the requisite microfluidic functionalization apparatus is developed for a particular cantilever array.

An alternative deposition technique that may be employed to selectively coat cantilevers with specific polymer sensing layers is matrix assisted pulsed laser evaporation (MAPLE). This technique involves dispersal of the target material in an organic host followed by evaporation in vacuum with a pulsed laser. This method is a generic process that has successfully deposited thin films of a wide range of chemoselective materials, including highly adsorptive chemoselective polymers. MAPLE permits precise control over polymer deposition thickness with a high degree of uniformity, and retains all the original physicochemical properties of the chemoselective polymer. Also, MAPLE allows for localized coating deposition using non-contact shadow masking with micron-sized features that meet the required dimensions of the cantilever technology. Arrayed cantilever sensors can be coated with different polymers employing multiple targets in the MAPLE deposition chamber and a moveable shadow mask. In a manufacturing process many sensor array chips can be simultaneously coated with a high degree of control.

Bending and resonance frequency shifts of a cantilever are typically measured using techniques perfected for atomic force microscopy. These include optical reflection, piezoresistive, capacitive, and piezoelectric methods. However, these methods are not easily adapted for detection of cantilever motion in microcantilever sensor arrays. For example, the laser-beam reflection technique is quite sensitive but does not scale well as the number of microcantilevers in an array becomes large. The piezoresistive method has less measurement sensitivity but is amenable to standard microprocessing techniques for large number of cantilevers. However, the piezoresistive method cannot be easily adapted to liquid ambients. The capacitive method measures changes in capacitance between the cantilever and an adjacent surface, yet this close proximity causes complications due to electrostatic interactions that lead to stiction, among other issues. Therefore there is a need in the art for development of microcantilever sensors that may be amenable to miniaturization and scalable to an array of microcantilevers on a single chip. Additionally, there is also a need in the art for a microcantilever sensor that is suitable in both vapor and liquid environments, and therefore new methods of detecting microcantilever motion must be developed.

BRIEF SUMMARY OF THE INVENTION

According to one embodiment of the invention, a microcantilever sensing system comprises a waveguide cantilever that permits an optical signal to propagate through an endface of the cantilever. The propagated signal is received by a receiver waveguide across a gap from the cantilever. The receiver waveguide provides the optical signal to a differential beamsplitter. The signal is split according to the position of optical light incident upon the receiving waveguide. According to one aspect of the invention the splitting is achieved through an asymmetrical strip load disposed on the receiver waveguide and a y-beamsplitter. The strip load is disposed on the receiver waveguide asymmetrically with respect to the waveguide branches, and typically comprises a material having a refractive index different from a refractive index of the receiver waveguide.

According to another aspect of the invention, the gap between the receiver and cantilever has a length so as to form a Fabry-Perot cavity of reflection therebetween. The Fabry-Perot cavity therefore permits establishing a distance therebetween to result in a destructive interference of optical signals reflected across the gap. Other aspects of the invention include grating couplers disposed on the input or output waveguides to the system. Such a coupler permits receiving and providing the optical signals to and from optical fibers, such that the optical signal may be processed. Yet another aspect of the invention includes reducing the dimensions of the microcantilever sensing system by including waveguide bend mirrors upon the input waveguides or the output waveguides. These waveguide bend mirrors may comprise an air trench mirror.

The microcantilever sensing system may advantageously be employed in sensing systems comprising an analyte for detecting vapors or liquids, such as described in the background. In these embodiments, therefore, the analyte may be disposed upon the waveguide cantilever. As such, the microcantilever system may be employed to determine the deflection of the cantilever and thus the adsorption of the analyte.

Another embodiment of the invention comprises an array of waveguide microcantilevers, as described above, that includes an optical signal source and a plurality of beamsplitters for splitting the optical signal to different waveguide branches. The waveguide branches ultimately provide each of the waveguide cantilevers in the array a portion of the optical signal for processing as above.

Another embodiment of the invention includes a method of determining a deflection of a waveguide of the microcantilever. An optical signal is transmitted from the endface of a waveguide microcantilever and received by the receiver waveguide. The optical signal is differentially split and then each split signal is compared to determine beam deflection. The differential split may be an occurrence caused by the asymmetrical strip load, as described above.

Yet another embodiment of the invention is a method of fabricating a microcantilever sensor. An optically transparent layer is disposed on a clad and substrate and patterned to provide a y-beamsplitter having an input waveguide and two output waveguide branches. A cantilever is etched into the input waveguide to form a gap in the input waveguide, thus creating the receiver waveguide opposed to the cantilever. A strip load of different refractive index material is asymmetrically disposed over a portion of the receiver waveguide. The cantilever is released from the substrate by etching the clad under the cantilever. An overclad may then be disposed on at least a portion of the optically transparent layer.

BRIEF DESCRIPTION OF THE SEVERAL VIEWS OF THE DRAWINGS

Having thus described the invention in general terms, reference will now be made to the accompanying drawings, which are not necessarily drawn to scale, and wherein:

DETAILED DESCRIPTION OF THE INVENTION

The inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

According to embodiments of the invention, a microcantilever sensing system includes a waveguide microcantilever with differential beamsplitter permitting differential optical readout to meet the needs described in the background. Moreover, a microcantilever sensing system may be integrated at the chip level with the cantilevers such that embodiments of the invention lends itself to batch fabrication. According to embodiments of the invention, a waveguide microcantilever includes a receiver waveguide and differential beamsplitter for differential detection of transmitted light and integration with other optical components. Waveguide structures have been developed to enable the microcantilever sensing system to be reduced in size and these structures are described in commonly assigned co-pending application entitled "Planar Lightwave Circuit Waveguide Bends and Beamsplitters," application Ser. No. 60/514,030, incorporated herein in its entirety by reference. As a result, the invention may lead to overall microcantilever sensor size reduction and be more scalable to an array of microcantilevers on a chip.

Figure 1A:
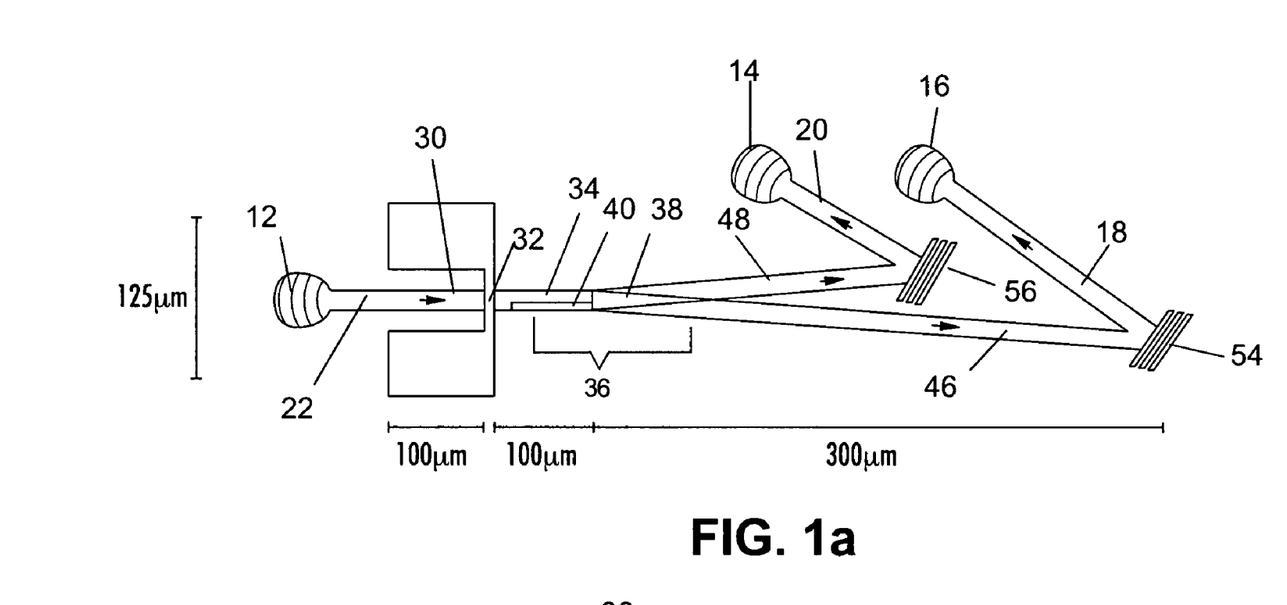
FIG. 1(a) is a schematic of a microcantilever sensing system comprising a waveguide microcantilever with differential beamsplitter according to one embodiment of the invention.
Figure 1B:
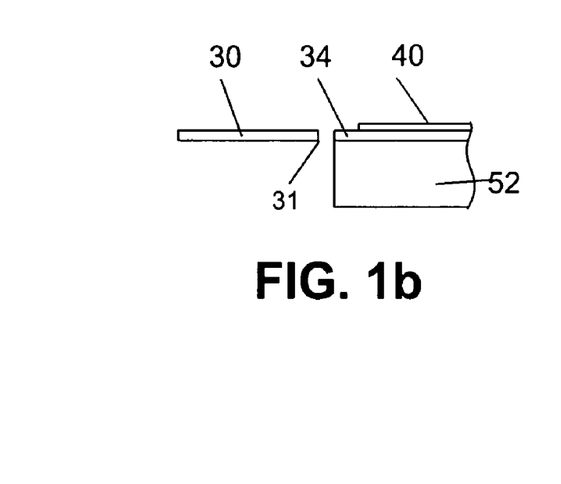
FIG. 1(b) is a side view of a waveguide microcantilever illustrated in FIG. 1(a) and according to one embodiment of the invention.
Figure 1C:
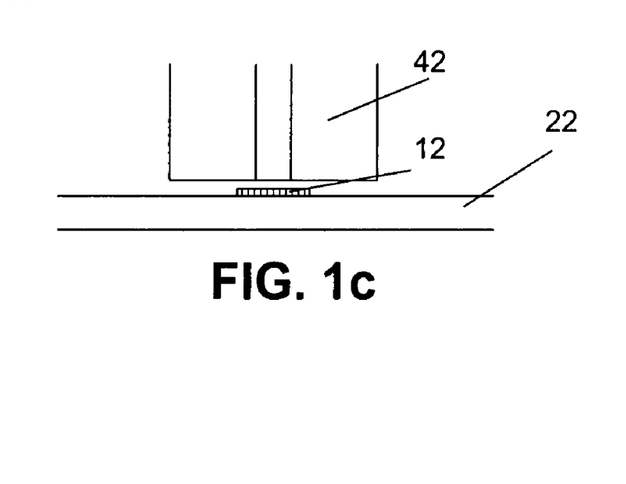
FIG. 1(c) is a side view of a fiber and grating coupler for a waveguide microcantilever according to one embodiment of the invention.

Referring now to FIGS. 1(a)–(c), a schematic illustration of one embodiment of a microcantilever sensing system is depicted. A grating coupler 12 couples light from the fiber into a waveguide 22 that continues along the extent of the cantilever 30. Light exits the waveguide cantilever 30 at an endface 31 (FIG. 1(b)) adjacent a small gap 32 (for example ~1–5 μm) and propagates across to the receiver waveguide 34. Following the receiver waveguide 34, a differential beam splitter 36, splits the light according to deflection of the cantilever. The differential beamsplitter, according to this embodiment, comprises a Y-beamsplitter 38 having asymmetrical strip load 40 on the receiver waveguide 34 of a different refractive index material so that light entering it is split into two separate output waveguide branches 46, 48. The strip load 40 is asymmetrical about the top plane of the waveguide 34 and waveguide branches 46, 48 such that the beam is split with a ratio dependent on the vertical position of the incident light on the waveguide 34. Thus, light propagated to each branch of the beamsplitter 38 is differential based upon the vertical position of the cantilever endface 31 with respect to the receiver waveguide 34. The two output waveguide branches 46, 48 from the Y-beamsplitter are folded by air trench mirrors 54, 56 such as described in the previously incorporated co-pending application. The air trench mirrors permit a more compact sensor, and without the bends the system could be an additional 500 μm long.

The optical signals may be supplied to and from the microcantilever sensing system interconnected to optical fibers via grating couplers 42. FIG. 1(c) illustrates an optical fiber 42 mounted above an input grating 12. Light is coupled into and out of optical waveguide 22 using a grating coupler 12 such that optical fibers 42 can be mounted normal to the waveguide 22 plane. Likewise, output grating couplers 14, 16 (FIG. 1(a)) operate on the same principle. Grating couplers 14, 16 direct light out of the output waveguides and into optical fibers that are connected to detectors in the reverse operation as FIG. 1(*c*). Signals from these detectors may be differentially compared to measure deflection. Typically, light with a wavelength of 1.3 µm or 1.55 µm can be used to readout the waveguide cantilevers.

Figure 2A:
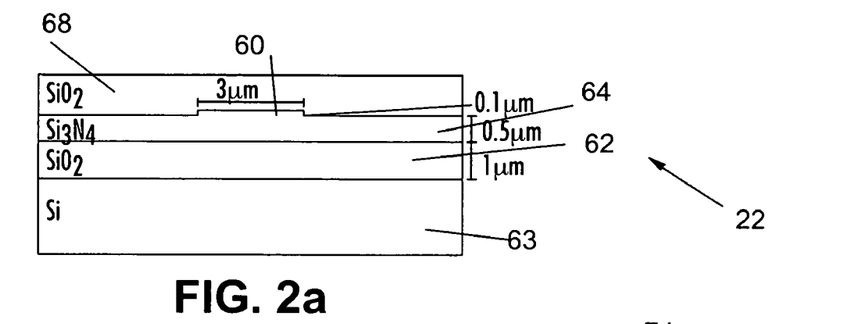
FIGS. 2(a) and 2(b) are cross-sections of transmitting waveguides on a substrate and cantilever, respectively, of a waveguide microcantilever according to one embodiment of the invention.

A waveguide cantilever of a microcantilever sensing system may include waveguides comprising either single crystal silicon or low stress-silicon nitride, or other optically transparent materials. For example, referring to FIG. 2(*a*) a cross-section of a waveguide comprising low stress silicon nitride is disposed upon of a Si wafer 63 coated with both an oxide layer 62 and a nitride layer 64. The oxide layer 62 operates as the waveguide clad. A waveguide 60 is formed by etching a shallow ridge in the nitride layer 64. The resulting ridge waveguide 60 supports low loss propagation. The oxide overclad 68 is used to reduce scattering loss for the waveguide bend and beamsplitter structures that are discussed below.

Figure 2B:
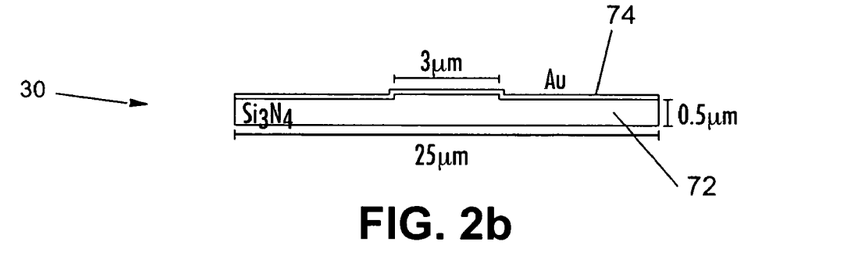

According to one embodiment of the invention, a cantilever waveguide 30 is shown in FIG. 2(*b*) and comprises a single layer of silicon nitride 72 to minimize initial-state deflection of the cantilever. A surface material that is conducive to carrying analytes upon the cantilever is also disposed thereon, and in this embodiment comprises gold 74. Chemo- or bioselective coatings may be applied to the top of the gold surface 74 of the cantilever. For many of these coatings a thin layer of gold 74 is first applied to promote film adhesion to only one side of the cantilever. These coatings will have some effect on the optical properties of the cantilever waveguide, but these are expected to be negligible in terms of system performance. For example, a gold coating will increase the optical loss in these waveguides, but since cantilevers are short (~100 µm) the effect on the loss budget is small. Also, polarization effects may be controlled by limiting the illumination to a single polarization state by polarization filtering with the waveguide bends to be discussed below.

Returning to FIG. 1(*a*), optical loss from propagation across the gap between the cantilever 30 tip and the receiver waveguide 34 occur from Fresnel reflection at the endface 31 of the cantilever and the entrance face of the receiver waveguide. Advantageously, these partially reflective surfaces form an effective Fabry-Perot cavity that can be tuned through choice of gap 32 length to achieve destructive interference of the reflected components thereby minimizing loss. It should be noted that both the nature of the waveguide cantilever and selection of the gap length permit cantilevers to operate in either vapor or liquid ambients.

Figures 3A, 3B:
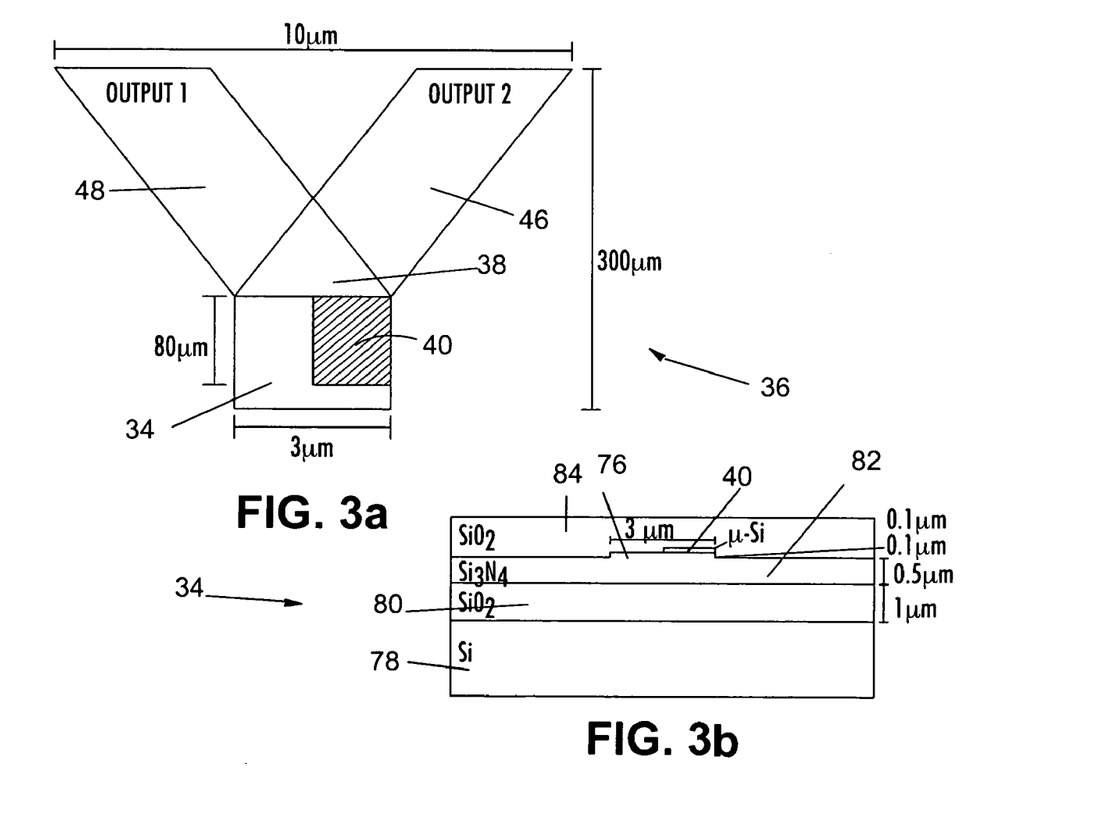
FIGS. 3(a) and 3(b) are top view and cross-section, respectively, of a receiving waveguide and differential beamsplitter of a waveguide microcantilever according to one embodiment of the invention.

A top view and cross section of the receiver waveguide 34 are shown in FIGS. 3(*a*) and (*b*). The receiver waveguide is optically connected to a differential beamsplitter. As used herein, differential beamsplitter refers to a beamsplitter that splits the light according to the position of light incident upon the receiver waveguide. The light is therefore directed to branches of the beamsplitter in different proportions, and differential therefore refers to the different proportions. Differential splitting may be achieved in several different ways. For example in this embodiment, a y-splitter 38 having strip loading 40 directs light in different proportions due to the position of the strip loading relative to each branch. The strip loading is a high refractive index material on one half of the common path. The asymmetric strip loading 40 causes the mode profile of the beam to shift relative to one or the other branches of the splitter. Thus, the beam is proportionally split into two output ports of the y-splitter 38 in a ratio dependent on the vertical position of the incident beam, which in turn is dependent on the cantilever 30 deflection. Note that except for the strip loading 40, the receiver waveguide design has the same waveguide ridge 76 height (0.1 µm). Similarly the same materials may be employed as previously described in conjunction with the cantilever waveguide 30, a substrate 78, an oxide layer 80, silicon nitride 82 with an etched waveguide ridge 76, and an oxide overclad 84. It may be advantageous to construct the receiver waveguide 34 in the same manner as the cantilever waveguide such that both waveguides can be fabricated in a single process. The strip loading 40 is disposed upon the waveguide ridge 76 and may include amorphous silicon in a section 80 µm long, beginning 20 µm from the entrance facet is sufficient to split the beams. After propagating 200 µm the y-splitter output waveguides 46, 48 are separated by a distance of ~4 µm.

According to one embodiment for fabricating a microcantilever waveguide sensing system with differential beamsplitter, the waveguides and cantilever may be manufactured on a silicon substrate 63, 78 having a 1.0 µm thick oxide layer 62, 80 grown or disposed thereon. A 0.6 µm layer of silicon nitride 64, 82, may be disposed to permit forming the waveguide. The waveguide ridges 60, 76 may be patterned with optical lithography and etched by reactive ion etching (RIE). At this point, the cantilever 30 and gap 32 may be etched in the nitride layer 64, 82. The strip loading amorphous silicon 40 may be deposited, patterned, and subsequently etched.

To fabricate the grating couplers on the same substrate, it may be advantageous to pattern and etch the layered grating structures prior to depositing the overclad oxide layers 68, 84. The air trenches 54, 56 may be etched into the waveguide using inductively coupled plasma reactive ion etching (ICP-RIE). Deep RIE (DRIE) may be employed to etch through backside of substrate underneath cantilever 30 to permit release of cantilevers by removing final $SiO_2$ layer. The analyte carrying material, such as gold in the previous embodiment, may be subsequently deposited.

It will be noted by one of ordinary skill in the art that optical cantilevers and sensing systems of the inventions herein are generally fabricated using standard semiconductor manufacturing techniques. Therefore, the fabrication is accomplished through standard monolithic semiconductor manufacturing techniques, including chemical vapor phase deposition techniques, physical vapor deposition or sputtering techniques, evaporation techniques, spin-on deposition techniques, photolithography, wet or dry etching techniques, etc. The specific fabrication technique is often chosen with respect to manufacturing equipment and materials used in the deposition. As such, the apparatus disclosed herein may be fabricated in conjunction with many techniques and materials, as will be recognized by one of ordinary skill in the art.

Additionally, FIGS. 2(*a*)–(*b*) and 3(*a*)–(*b*) illustrate relatively simple layers depicting a few semiconductor elements and optical elements, however, it is expected that multiple optical and semiconductor elements will be disposed within a single layer, and multiple layers of optical and semiconductor elements will be repeatedly designed and disposed upon other layers. It will be understood by those having ordinary skill in the art that when a layer or element is "disposed on" another layer or element, it may be formed directly on top, bottom or side surface area, or one or more intervening layers may be provided between the layers. The number of elements within a layer and the number of layers themselves are only constrained by the available manufacturing parameters, such as size requirements for the imaging and etching techniques, the area of the semiconductor substrate, and by the physical dimension limitations set for the circuit by the intended application of the circuit.

It should be noted that while the embodiments described herein appear to provide for specific layering, for example, constructing an oxide layer 62 prior to a nitride layer 64, it is possible to layer the device in any order that makes for efficient and reliable manufacturing. In other words, it is possible and within the inventive concepts disclosed herein to fabricate the device with additional layers, alternate layers, or combinations of other types of layers. In this regard, FIGS. 2(a)–(b) and 3(a)–(b) are examples of relatively simplistic fabrication configurations and related optic connectivities. It should be noted that other fabrication configurations and optic connectives are also feasible and are within the inventive concepts disclosed herein. The specific configuration and connectivity will be chosen to best match the performance requirements of a particular application.

According to one embodiment of a method for determining microcantilever beam deflection, differential signals (i.e., signals of different proportions) from the two output waveguides 46, 48 may be detected and normalized to measure deflection of the cantilever 30. This method provides the greatest sensitivity for small deflections of the cantilever tip and eliminates errors due to optical source noise. The normalized signal, or 'contrast', is written in terms of the photogenerated current at detectors associated with each of the output waveguides:

$$K=(I_1-I_2)/(I_1+I_2) \quad (7)$$

in which $I_1$ and $I_2$ are the currents measured at photodetectors coupled to the output optical fibers from y-splitter branches, 1 and 2, respectively. The current at a detector is a function of the optical power incident on its surface:

$$I_x=(e\eta_x P_x \lambda)/hc \quad (8)$$

where x=1, 2 corresponding to each detector, e is the electron charge, $\eta$ is the detector's quantum efficiency, $P_x$ is the power that reaches the detector, $\lambda$ is the laser's wavelength, h is Planck's constant, and c is the velocity of light in a vacuum.

Figure 4:
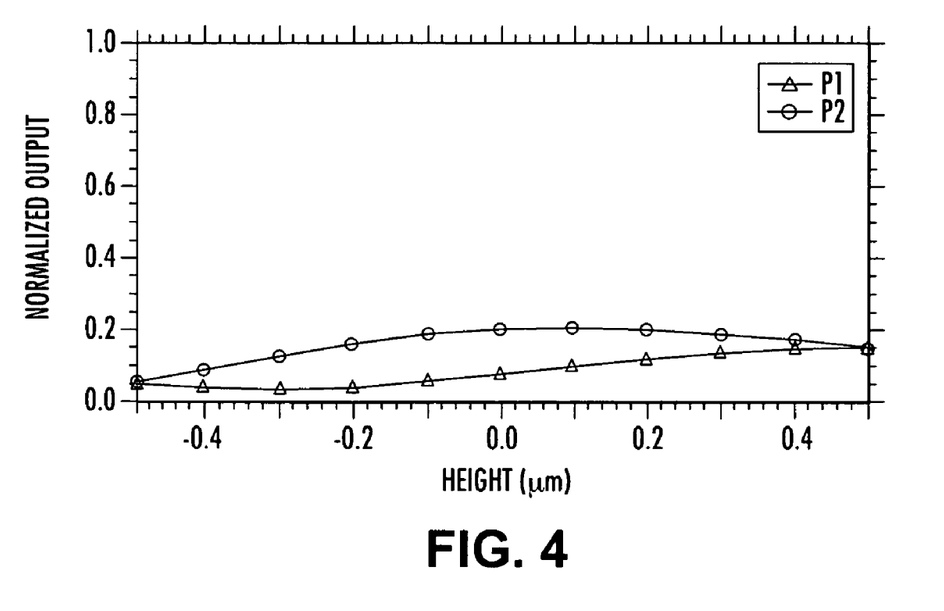
FIG. 4 is a plotted illustration of differential output of a microcantilever sensing system according to one embodiment of the invention.
Figure 5:
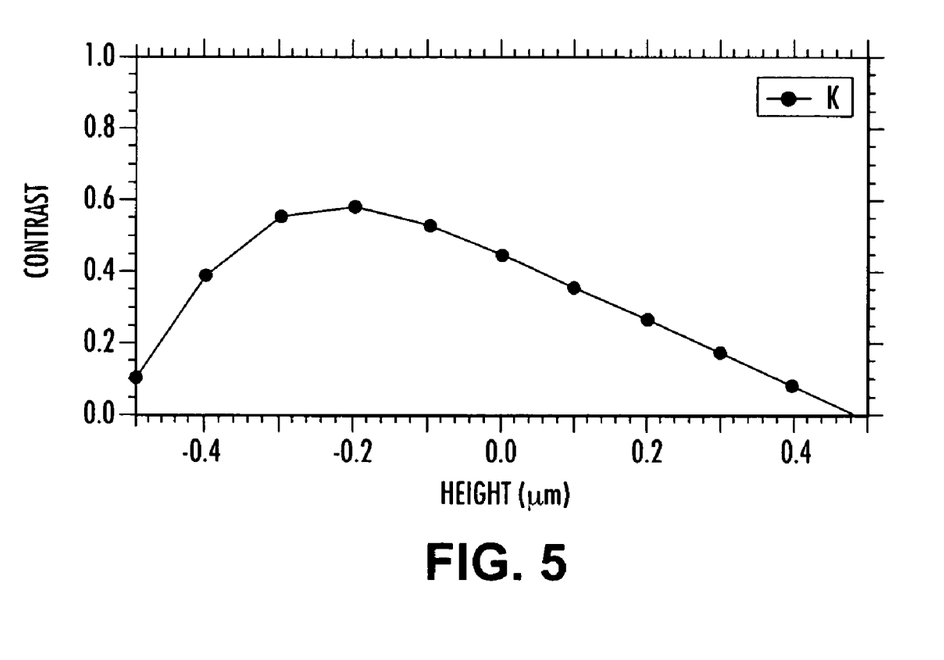
FIG. 5 is a plotted illustration of differential output contrast of a microcantilever sensing system according to one embodiment of the invention.

FIG. 4 illustrates the normalized resulting optical power in each output waveguide P1, P2 as a function of tip deflection from the horizontal axis. For each embodiment this may be determined empirically or by an algorithm such as a micro-genetic (µGA) algorithm with a 2-D finite difference time domain (FDTD) as described in Jiang and Nordin "A Rigorous Unidirectional Method for Designing Finite Aperture Diffractive Optical Elements," Optics Express, Vol. 7, 237–242 (2000), and in Jiang, Cai, Nordin, and Li "Parallel Microgenetic Algorithm Design for Photonic Crystal and Waveguide Structures," Optics Letters 28(23), 2381–2383 (2003); both of which are incorporated herein by reference. Other methods and algorithms may be used to design cantilevered waveguides, as described herein, and these algorithms are known to those of ordinary skill in the art and may be substituted without departing from the spirit or scope of the invention. The contrast can then be calculated from each output, P1, P2, and is shown in FIG. 5. In this particular embodiment, the contrast is linear in the range of −0.2 µm to 0.5 µm with a slope of −0.846 µm$^{-1}$. The linear range is sufficient for measuring small deflections that arise from surface stress changes due to molecular adsorption and absorption in chemo- and bio selective films. The use of low stress nitride or single crystal silicon as the cantilever material permits avoiding initial cantilever deflection outside of the measurement range. The linear range of the differential signal may be adjusted by changing the receiver waveguide design, such as changing the asymmetry of the strip loading.

One approach to coupling light into and out of the waveguides is to place optical fibers at normal incidence to the waveguide plane by way of a waveguide grating coupler as previously described in conjunction with FIG. 1(c). In one embodiment, a stratified grating coupler (SGC) was employed, and the SGC includes multiple binary grating layers shifted laterally with respect to one another. Shifting the grating layers emulates a volume holographic coupler with slanted fringes and permits a normal angle of incidence. Advantageously, SGCs may be fabricated using planar batch processes, which has been demonstrated with a stratified grating structure similar to an SGC for a high-efficiency transmission grating application.

Employing an algorithm, in this particular embodiment employing the previously mentioned µGA FDTD method, an SGC was developed to couple light from a single mode optical fiber into a single mode waveguide and differential beamsplitter. In this embodiment the optical mode is launched into the fiber. The optical mode propagts through the fiber and then interacts with the SGC and coupling into the waveguide. The input coupling was determined to be 64%, and simulation results for outcoupling efficiency (light propagating in the waveguide and coupled into the fiber) demonstrated similar efficiency.

Cantilever deflection sensitivity considerations include optical loss in propagating end-to-end through the system and limitations imposed by noise. These considerations determine the required input source power (and therefore the number of microcantilevers that can be optically supplied by a single fiber-coupled external optical source) and also the noise level in the detection process. For example, a loss budget table for one embodiment is illustrated below and identifies the sources of loss by a beam as it propagates through the sensor.

| Loss Origin | Magnitude (dB) |
|---|---|
| Fiber to Waveguide | 3–5 |
| Waveguide Propagation | 0.2 |
| Waveguide to Cantilever | 0.5 |
| Cantilever Propagation | 0.2 |
| Cantilever to Splitter | 1–2 |
| Splitter Propagation | 13 |
| Air trench Mirrors | 0.5 |
| Waveguide to Fiber | 3–5 |
| Total | 21.4–26.4 dB |

The loss budget must be considered in conjunction with an analysis of the noise performance. The fundamental limits of cantilever deflection sensitivity are understood by presuming shot noise as the most limiting factor. Examining changes in the contrast for small changes in detector current, and implying differentiation of contrast with respect to current, we find:

$$\Delta K = \frac{2(\Delta I_1 I_2 - \Delta I_2 I_1)}{(I_1+I_2)^2} \quad (9)$$

from equation (1). The standard deviation of shot noise-induced variations in the photogenerated current can then be represented as $$\sigma_x = \sqrt{\frac{2e^2 \eta_x B P_x \lambda}{hc}} \quad (10)$$

where x=1, 2 corresponding to detectors on each of the two output ports and B is the bandwidth. Assuming $\eta_1=\eta_2=\eta$, letting $\sigma_x=\Delta I_x$ and substituting equations (8) and (10) into (9), the result is $$\Delta K = \frac{\sqrt{8hc}\sqrt{\frac{B}{\lambda\eta}}(P_2\sqrt{P_1} - P_1\sqrt{P_2})}{(P_1+P_2)^2} \quad (11)$$

Assuming 10 µW coupled into the receiver waveguide and losses as in the table above, the power at the detectors for the deflection that results in the greatest shot noise (cantilever height=−0.2 µm, and determined empirically from µGA-FDTD, as above) is $P_1$=0.577 µW and $P_{2=0.151}$ µW. Inserting these values into equation (5), choosing a bandwidth of B=1 Khz η=0.75, and evaluating the expression we find ΔK=7.64×10$^{-6}$. While operating in the linear range of FIG. 5 contrast dependence on vertical position of the incident beam on the splitter is just K=my+b. Differentiating the contrast with respect to vertical position, the change in position may be expressed relative to a change in contrast as Δy=ΔK/m. The contrast change calculated as a result of a current change can be substituted to arrive at a value for the cantilever deflection noise level for this case, which is Δy=9.03 pm. The sensitivity of the tip deflection measurement is small, which permits measurements of chemical and biological analytes.

Figure 6:
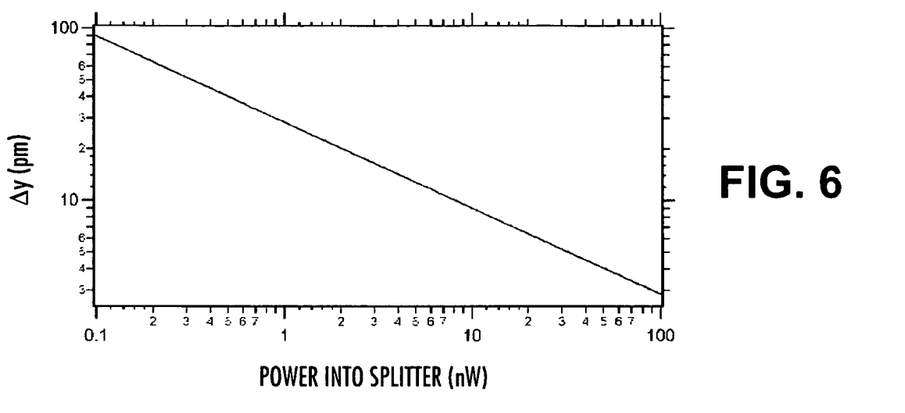
FIG. 6 is a graph illustrating deflection sensing for power input to a microcantilever sensing system according to one embodiment of the invention.

The above calculation presumes 10 µW coupled into the receiver waveguide. FIG. 6 shows the tip deflection sensitivity, Δy, as a function of optical power. The required source power may need to be only 6 dB higher than the amount of light coupled into the receiver waveguide considering the loss budget table. A single mW-scale optical source should be able to supply a large number of microcantilevers permitting the microcantilever sensing system to be scaled to large arrays.

Figure 7:
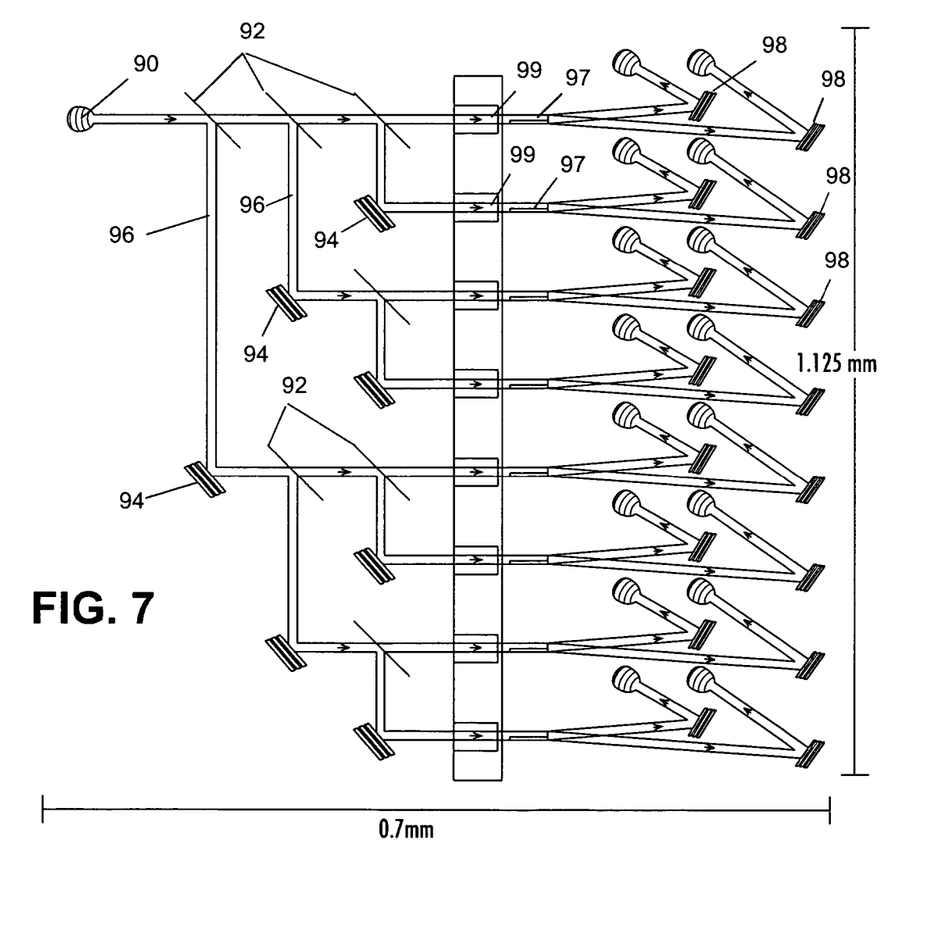
FIG. 7 is a schematic of a microcantilever sensing system comprising an array of waveguide microcantilevers according to two embodiments of the invention.

Referring to FIG. 7, and according to another embodiment of the invention, a microcantilever sensing system may be scaled to a large array and may comprise a network of waveguide branches 96 to permit light from a single fiber and grating coupler 90 to supply an array of waveguide cantilevers 99. The physical dimensions of a sensor array are dependent on the footprint needed for the waveguide bends and splitting junctions that comprise the network. Normally these components require several centimeters of chip space to implement because large radius bends are necessary to avoid substantial power leakage out of the waveguide in a bend.

To reduce the chip space necessary to accommodate the microcantilever sensing system may employ air trench waveguide bends 94, 98 and air trench beamsplitters 92 that spilt light to pluralities of waveguide microcantilevers 99. The operation of the waveguide microcantilevers 99 and differential beamsplitters 97 are substantially the same as described above, and may be fabricated as described above.

FIG. 7 therefore illustrates extending the concept to a branch structure for 8 cantilevers. These embodiments may be scaled to a $2^n$ splitting array. For beamsplitters 92 with a 50/50 splitting ratio and high efficiency mirrors, the optical power at the output of each branch is equal.

High efficiency sharp angle bends and beamsplitters are disclosed in co-pending U.S. patent pplication Ser. No. 60/514,030 previously incorporated in its entirety herein by reference. For sharp angle bends an air trench is placed at the corner of a 90° waveguide bend to reflect an incident beam into the output waveguide. For beamsplitters an air trench is placed 45° to the incident beam to split the light evenly into two output waveguides. The air trenches permit total internal reflection and frustrated total internal reflection. The air trench discussed herein is compatible with fabrication of the other components of the waveguide cantilever sensor, however, other types of bends and beamsplitters may be substituted therefor without departing from the spirit or scope of the invention.

In a three air trench embodiment, the air trenches 94 may be etched into the material stack and include planar vertical interfaces. In one particular embodiment used for analysis, the core and clad refractive indices are 1.500 and 1.465 respectively, and the waveguide width is 2 µm. For light with a free space wavelength, $\lambda_0$, of 1.55 µm, the waveguide supports a single transverse mode. The previously identified µGA-FDTD design method was employed to design this air trench bend, or other algorithms known to those of ordinary skill in the art, may be employed to optimize the trench lengths, trench thicknesses, trench separation, and the overall position of the trenches relative to the waveguide. The µGA-FDTD analysis for this embodiment yielded thicknesses of the air trenches that are significantly different (1.05 µm for the first, 0.52 µm for the second, and 0.70 µm for the third). As a result the optical signal launched into the input waveguide and reflected into the output waveguide had an efficiency of 97.2%.

A waveguide beamsplitter 92 can be formed with a single air trench that is designed to work by frustrated total internal reflection. In one embodiment, the µGA-FDTD design tool was employed to optimize the trench position, thickness, and length. According to one embodiment, the trench is 10.5 µm long and 0.39 µm thick shifted by 0.38 µm along the +x-axis such that 48.8% of the incident light is transmitted and 49.7% is reflected for a total efficiency of 98.5%. The shift of the trench position accounts for the Goos-Hanchen shift, a shift in the phase of the reflected light dependent upon the transmission mode and angle of incidence of the light. Additional design parameters and methods are disclosed in the incorporated co-pending application, and one of ordinary skill in the art will recognize several alternative embodiments that may be employed herein.

The dimensions of an individual waveguide cantilever sensor with associated optical elements can be as small as 500 µm by 200 µm. The array spacing is limited by the diameter of the optical fibers and the placement of grating couplers such that there is no overlap with the waveguides in the adjacent sensor. The waveguides of the branching network need only be long enough that there is sufficient room to fabricate the air trench mirrors and beamsplitters. As a result, a microcantilever sensor system array of the invention can be fabricated in a relatively small area. For example, in the embodiment of an array with 8 cantilevers 99, as shown in FIG. 7 and a typical fiber diameter of 125 µm while allowing a small distance between fibers, the dimension of the array perpendicular to the cantilever may be on the order of 1.125 mm. The dimension parallel to the cantilever waveguides can easily be 0.7 mm.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A microcantilever sensing system having at least one microcantilever sensor, said microcantilever sensor comprising:
   a waveguide cantilever permitting an optical signal to propagate through an endface of the cantilever; and
   a receiver waveguide in optical communication with the waveguide cantilever endface such that the optical signal is communicated between the waveguide cantilever and the receiver waveguide; and
   a differential beamsplitter for splitting the optical signal based on a deflection of the waveguide cantilever.

2. The microcantilever sensing system according to claim 1, wherein the differential beamsplitter comprises an asymmetrical strip load disposed on the receiver waveguide and a y-beamsplitter comprising two waveguide branches for receiving portions of the optical signal, the strip load being asymmetrical with respect to the waveguide branches.

3. The microcantilever sensing system according to claim 2, wherein the strip load comprises a material having a refractive index different from a refractive index of the receiver waveguide.

4. The microcantilever sensing system according to claim 1, wherein a gap is defined between the waveguide cantilever endface and the receiver waveguide.

5. The microcantilever sensing system according to claim 4, wherein the gap has a length between the receiver waveguide and the cantilever lever endface defined by a width permitting destructive interference of the optical signals reflected across the gap.

6. The microcantilever sensing system according to claim 1, further comprising two waveguide branches connecting outputs of the differential beam splitter.

7. The microcantilever sensing system according to claim 6, further comprising a grating coupler disposed on at least one of the two waveguide branches.

8. The microcantilever sensing system according to claim 6, further comprising a waveguide bend mirror disposed in a path of the optical signal of at least one of the two waveguide branches, the waveguide bend mirror reflecting the optical signal in a direction different than a direction of the waveguide branch.

9. The microcantilever sensing system according to claim 8, wherein the waveguide bend mirror has at least one trench.

10. The microcantilever sensing system according to claim 7, further comprising an optical fiber in optical communication with the grating coupler for receiving the optical signal from the grating coupler.

11. The microcantilever sensing system according to claim 1, further comprising a grating coupler in optical communication with the waveguide microcantilever for providing the optical signal to the waveguide microcantilever.

12. The microcantilever sensing system according to claim 11, further comprising an optical fiber in optical communication with the grating coupler for providing the optical signal to the grating coupler.

13. The microcantilever sensing system according to claim 1, further comprising an analyte carrier disposed on the waveguide microcantilever.

14. The microcantilever sensing system according to claim 13, wherein the analyte carrier comprises gold.

15. A microcantilever sensing system, comprising:
   an optical signal source for providing an optical signal;
   a plurality of beamsplitters for splitting the optical signal into portions;
   a plurality of waveguide branches for receiving a portion of the split optical signal; and
   a plurality of waveguide microcantilever sensors, each microcantilever sensor receiving the respective portion of the optical signal from at least one of the plurality of beamsplitters, each microcantilever sensor comprising,
      a waveguide cantilever permitting the portion of the optical signal to propagate through an endface of the cantilever;
      a receiver waveguide in optical communication with the waveguide cantilever endface such that the portion of the optical signal is communicated between the waveguide cantilever and the receiver waveguide; and
      a differential beamsplitter for splitting the optical signal based on a deflection of the waveguide cantilever.

16. The microcantilever sensing system according to claim 15, wherein the differential beamsplitter comprises an asymmetrical strip load disposed on the receiver waveguide and a y-beamsplitter comprising at least two waveguide branches for receiving portions of the optical signal, the strip load being asymmetrical with respect to the waveguide branches.

17. The microcantilever sensing system according to claim 16, wherein the strip load comprises a material having a refractive index different from a refractive index of the receiver waveguide.

18. The microcantilever sensing according to claim 15, wherein a gap is defined between the waveguide cantilever endface and the receiver waveguide.

19. The microcantilever sensing system according to claim 18, wherein the gap has a length between the receiver waveguide and the cantilever endface defined by a width permitting destructive interference of the optical signals reflected across the gap.

20. The microcantilever sensing system according to claim 15, further comprising two waveguide branches connecting outputs of the differential beam splitter.

21. The microcantilever sensing system according to claim 20, further comprising a waveguide bend mirror disposed in a path of the optical signal of at least one of the two waveguide branches, the waveguide bend mirror reflecting the optical signal in a direction different than a direction of the waveguide branch.

22. The microcantilever sensing system according to claim 15, further comprising an analyte carrier disposed on the waveguide microcantilever.

23. A method of determining a deflection of a waveguide microcantilever, comprising:
   transmitting an optical signal from an endface of a waveguide microcantilever;
   receiving the transmitted optical signal;
   differentially splitting the transmitted optical signal;

comparing the power of each of the differentially split signals; and determining microcantilever beam deflection based upon the comparison of power.

24. The method according to claim 23, further comprising detecting each of the differentially split signals with a photodetector to convert the power output to current representative of the power output.

25. The method according to claim 23, wherein the step of comparison comprises determining the contrast of the differentially split signals.

26. The method according to claim 25, wherein the step of determining the contrast comprises calculating a normalized ratio of power outputs.

27. The method according to claim 23, wherein the step of differentially splitting the transmitted optical signal comprises proportionally splitting the signal by changing the optical signal mode profile in relation to branches of a beamsplitter.

28. The method according to claim 27, wherein the step of proportionally splitting the signal by changing the optical signal mode profile with strip loading asymmetrically disposed on the beamsplitter input relative to each branch of the beamsplitter.

29. A method of determining analyte adsorption, the analyte being disposed upon the waveguide microcantilever, comprising:

transmitting an optical signal from an endface of a waveguide microcantilever;

receiving the transmitted optical signal;

differentially splitting the transmitted optical signal;

comparing the power of each of the differentially split signals; and determining analyte adsorption based upon the comparison of power.

30. The method according to claim 29, further comprising detecting each of the differentially split signals with a photodetector to convert the power output to current representative of the power output.

31. The method according to claim 29, wherein the step of comparison comprises determining the contrast of the differentially split signals.

32. The method according to claim 31, wherein the step of determining the contrast comprises calculating a normalized ratio of power outputs.

33. The method according to claim 29, wherein the step of differentially splitting the transmitted optical signal comprises proportionally splitting the signal by changing the optical signal mode profile in relation to branches of a beamsplitter.

34. The method according to claim 33, wherein the step of splitting the signal by changing the optical signal mode profile with strip loading asymmetrically disposed on the beamsplitter input relative to each branch of the beamsplitter.

35. The method according to claim 29, further comprising sensing a change in the analyte adsorption based on the determining.

36. A microcantilever sensing system having at least one microcantilever sensor, said microcantilever sensor comprising:

a cantilever having a first waveguide;

a second waveguide positioned to optically communicate with the first waveguide; and a differential beamsplitter positioned within a path of an optical signal communicated between the first waveguide and the second waveguide such that the differential beamsplitter receives and differentially splits the optical signal after communication of the optical signal between the first and second waveguides.

37. The microcantilever system according to claim 36, wherein a gap is defined between the first and second waveguides.

38. A method for use in a microcantilever sensor, comprising:

communicating an optical signal between a first waveguide and a second waveguide, the first waveguide on a cantilever of the sensor;

differentially splitting the optical signal into at least a first split signal and second spilt signal; and determining a deflection of the cantilever based on the first and second split signals.

39. The method according to claim 38, wherein the determining comprises comparing a power of the first split signal and a power of the second split signal.

40. The method according to claim 38, wherein a gap separates an endface of the first waveguide and an endface of the second waveguide.

* * * * *